(12) United States Patent
Short et al.

(10) Patent No.: US 8,182,430 B2
(45) Date of Patent: May 22, 2012

(54) THERMOCROMATIC PATCH FOR MONITORING/DETECTING BODY TEMPERATURE

(75) Inventors: Dan C. Short, Paris, KY (US); Albert B. Ouimet, Lexington, KY (US); Bryan S. Short, Lexington, KY (US)

(73) Assignee: Hot Dot, Inc., Lincoln, NE (US)

( * ) Notice: Subject to any disclaimer, the term of this patent is extended or adjusted under 35 U.S.C. 154(b) by 28 days.

(21) Appl. No.: 12/505,176

(22) Filed: Jul. 17, 2009

(65) Prior Publication Data

US 2010/0268112 A1  Oct. 21, 2010

Related U.S. Application Data

(60) Provisional application No. 61/171,252, filed on Apr. 21, 2009.

(51) Int. Cl.
*A61B 5/00* (2006.01)
*G01K 11/00* (2006.01)
(52) U.S. Cl. .......................... 600/549; 374/162
(58) Field of Classification Search .......... 600/549; 374/159–162, 100, 210
See application file for complete search history.

(56) References Cited

U.S. PATENT DOCUMENTS

| | | | |
|---|---|---|---|
| 3,661,142 A * | 5/1972 | Flam | 374/162 |
| 4,524,778 A * | 6/1985 | Brown et al. | 600/549 |
| 5,622,137 A | 4/1997 | Lupton, Jr. et al. | |
| 5,895,658 A * | 4/1999 | Fossel | 424/401 |
| 2003/0040679 A1 | 2/2003 | Weber et al. | |
| 2005/0113654 A1 | 5/2005 | Weber et al. | |
| 2008/0161715 A1 * | 7/2008 | Stivoric et al. | 600/549 |
| 2008/0279253 A1 | 11/2008 | MacDonald et al. | |
| 2009/0046760 A1 | 2/2009 | Matheson | |
| 2009/0143516 A1 * | 6/2009 | MacDonald et al. | 524/236 |

FOREIGN PATENT DOCUMENTS

JP  61257905 A  * 11/1986

OTHER PUBLICATIONS

English Abstract of JP 61257905 A. JPO. 1986. pp. 1-2.*

* cited by examiner

*Primary Examiner* — Max Hindenburg
*Assistant Examiner* — John Pani
(74) *Attorney, Agent, or Firm* — King & Schickli, PLLC

(57) ABSTRACT

A thermocromatic device for detecting body temperature includes a substrate treated with a thermocromatic composition. The thermocromatic composition includes a thermocromatic agent that changes color at a predetermined temperature indicative of a condition to be detected.

13 Claims, 1 Drawing Sheet

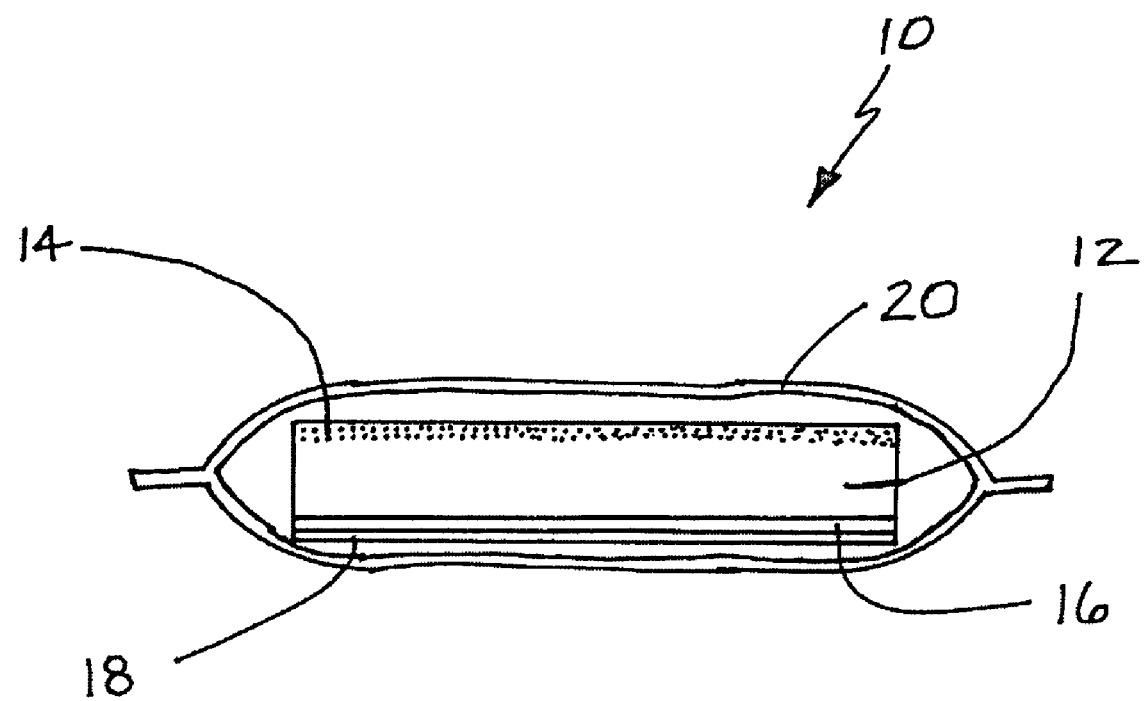

THERMOCROMATIC PATCH FOR MONITORING/DETECTING BODY TEMPERATURE

This application claims the benefit of U.S. Provisional Patent Application Ser. No. 61/171,252 filed on Apr. 21, 2009, the entire disclosure of which is incorporated herein by reference.

TECHNICAL FIELD

The present invention relates generally to thermocromatic devices and, more particularly, to such a device for detecting/monitoring body temperature in an accurate, efficient and inexpensive manner.

BACKGROUND OF THE INVENTION

The present invention relates to a thermocromatic device for monitoring body temperature. Such a device incorporates a thermocromatic ink developed to indicate, by changing color, a point where a preset temperature has been reached. Thermocromatic inks are nanoencapsulated and are extremely accurate. They also provide an efficient and inexpensive means to monitor body temperature.

Such devices have a number of uses. For example, a thermocromatic device incorporating a thermocromatic ink that changes temperature in a range of from 99° F. to 101° F. can be used to predict the point where a human's body core temperature has begun to reach a dangerous level. Upon noting a change in color of the thermocromatic device, the individual wearing the device may be removed from ongoing physical activity before suffering from heat stroke. This benefits athletes, hikers, those in the military and anyone in an environment creating risk of hyperthermia or hypothermia.

The thermocromatic devices are also useful for many other applications including but not limited to monitoring temperature to determine when a woman is ovulating, monitoring temperature to determine when another animal such as a horse is ovulating, determining when an animal such as a racehorse is in danger of overheating and undergoing heat exhaustion/heat stress, or even as a thermographic device. Such thermographic devices are useful as an aid (a) in diagnosing long term pain, deep vein thrombosis and conditions that affect peripheral circulation as well as (b) in the detection of tumors.

SUMMARY OF THE INVENTION

In accordance with the purposes of the present invention as described herein, a thermocromatic device is provided for detecting body temperature. The device comprises a substrate and a thermocromatic composition on the substrate. The thermocromatic composition includes a thermocromatic agent that changes color to a predetermined color indicative of a temperature related condition to be detected. The thermocromatic device may also include an adhesive for positively securing the substrate to the skin on the body to be monitored. The thermocromatic composition includes between about 0.1 and about 5.0 weight percent thermocromatic agent, between about 0.5 and about 1.0 weight percent negatively charged ionizing agent and the remainder carrier.

The thermocromatic agent is selected from a group consisting of a thermocromatic ink, a thermocromatic liquid crystal ink, a chiro nematic liquid crystal ink, cholesteryl nonanoate, a cyanobisphenyl, a combination of cholesteryl and nematic inks, a mixture of leuco dyes with a weak acid, a mixture of crystal violet lactone, a spirolactone, a fluoran, a spiropyran, a fulgide, or a fulgide with bisphenol A, a paraben, octadecylphosphoric acid, a 1,2,3-triazole derivative or 4-hydroxycoumarin, a mineral oxide, zinc oxide, lead oxide, cuprous mercury iodide, mercury iodide, nickel sulfate, a chromium rich pyrope, a chrystalline bismuth oxychloride, an organosiloxane containing methacryloyl or acryloyl functional groups, an organosiloxane containing nuclei that are divalent radicals consisting of 1,4 phenylene, 1,4 cyclohexylene, 2,2 pyridinylene, 2,5 pyranylene, 5,2 pyrimidinylene, 2,5-(1,3-dioxanylene), 2,6-naphthylidene and 1,4-naphylidene and combinations thereof. The substrate may be woven, knit or non-woven. The substrate may be made from a material selected from a group consisting of a natural fiber, a synthetic fiber, cotton, polyester, nylon, rayon, silk, wool, cotton blends, polyester blends and mixtures thereof. The adhesive may be selected from a group consisting of flexible silicones, epoxies, acrylics, and mixtures thereof.

Still further, the substrate may take a number of forms including, but not limited to, a patch, a scarf, a shirt, a headband, a wristband, a sweatband, a t-shirt, a compression jersey, a necklace and a pair of compression shorts. The predetermined temperature at which the thermocromatic agent changes color is typically between 95° F. and 105° F. Depending upon the particular application, the predetermined temperature may be in any one of the following ranges 99°-101° F., 100°-101° F., about 100° F., 95°-97° F., and about 96° F. The negatively charged ionizing agent may be selected from a group consisting of diatomaceous earth, hydrated aluminosilicate minerals, zeolite, choline chloride, modified polyolefins and mixtures thereof. The carrier may be selected from a group consisting of water, alcohol, polyols, phthlates and mixtures thereof.

In accordance with yet another aspect of the present invention, a method of monitoring body temperatures in animals is provided. That method comprises positioning a thermocromatic device into intimate contact with skin of the animal wherein the thermocromatic device changes color to a predetermined temperature indicative of a temperature related physical condition to be detected.

In accordance with additional aspects of the method, the method may also include the step of adhering the thermocromatic device to the skin. In an alternative approach the method includes elastically biasing the thermocromatic device into close engagement with the skin. Further, the method may include using a flexible substrate in the thermocromatic device capable of following the surface of the skin during bodily movements In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings:

FIG. 1 illustrates one possible embodiment of the present invention comprising a patch treated with a thermocromatic composition that changes color at a predetermined temperature indicative of a temperature related condition to be detected.

Reference will now be made in detail to the present preferred embodiment of the invention, examples of which are illustrated in the accompanying drawings.

DETAILED DESCRIPTION OF THE PREFERRED EMBODIMENTS OF THE INVENTION

As illustrated in FIG. 1, the present invention relates to a thermocromatic device 10 comprising a substrate 12 treated with a thermocromatic composition illustrated at 14. The device 10 may also include an optional adhesive layer 16. The substrate 12 typically comprises a textile structure which may be woven, knit or even non-woven. The substrate 12 may be made from a natural fiber, a synthetic fiber, cotton, polyester, nylon, rayon, silk, wool, cotton blends, polyester blends and mixtures thereof typically utilized by the textile and medical industries. In the illustrated embodiment, the substrate 12 takes the form of a patch. It should be appreciated, however, the substrate 12 may take a number of other forms including but not limited to a scarf, a shirt, a headband, a wristband, a sweatband, a t-shirt, a compression jersey, a necklace or even a pair of compression shorts.

The thermocromatic composition 14 is engineered to change color at a predetermined color indicative of a condition to be detected. The thermocromatic composition 14 includes between about 0.1 and about 5.0 weight percent thermocromatic agent, between about 0.5 and about 1.0 weight percent negatively charged ionizing agent and the remainder carrier. Typically, the thermocromatic composition is applied at a rate to provide between 1-2 mils dry thickness.

The thermocromatic agent is selected from a group consisting of a thermocromatic ink, a thermocromatic liquid crystal ink, a chiro nematic liquid crystal ink, cholesteryl nonanoate, a cyanobisphenyl, a combination of sholesteryl and nematic inks, a mixture of leuco dyes with a weak acid, a mixture of crystal violet lactone, a spirolactone, a fluoran, a spiropyran, a fulgide or a fulgide with bisphenol A, a paraben, octadecylphosphoric acid, a 1,2,3-triazole derivative or 4-hydroxycoumarin, a mineral oxide, zinc oxide, lead oxide, cuprous mercury iodide, mercury iodide, nickel sulfate, a chromium rich pyrope, a chrystalline bismuth oxychloride, an organosiloxane containing methacryloyl or acryloyl functional groups, an organosiloxane containing nuclei that are divalent radicals consisting of 1,4 phenylene, 1,4 cyclohexylene, 2,2 pyridinylene, 2,5 pyranylene, 5,2 pyrimidinylene, 2,5-(1,3-dioxanylene), 2,6-naphthylidene and 1,4-naphylidene and combinations thereof.

The negatively charged ionizing agent may be selected from a group consisting of diatomaceous earth, hydrated aluminosilicate minerals, zeolite, choline chloride, modified polyolefins and mixtures thereof. This list is not all inclusive as substantially any compounds capable of providing negatively charged ions may be utilized. The negatively charged ionizing agents provide the presence of increased oxygen due to increased blood flow at the site of the device 10. This increased level of blood and oxygen increases sensitivity of the thermocromatic device and more particularly, the thermocromatic agent thus providing for more effective monitoring of body temperature. Carriers useful for use in the present invention include, but are not limited to water, alcohols, polyols, phthlates and mixtures thereof.

The adhesive layer may comprise substantially any adhesive useful for securing the device to the skin so that the device stays in place during physical activity even in the presence of sweat, moisture, dirt and water. Some adhesives useful for forming the adhesive layer 16 include but are not limited to flexible silicones, epoxies and acrylics as well as mixtures thereof. A release paper 18 such as a silicone release paper can be used to cover the adhesive layer 16 prior to application. An outer wrapper 20 may be provided for packaging purposes. In order to use the device, one tears open the outer packaging 20, removes the release paper 18 and sticks the device 10 on the skin by placing the device over the desired area and pressing down on the device compressing the adhesive layer 16 against the skin.

The device 10 is relatively easy to manufacture. The substrate 12 is impregnated with the thermocromatic composition 14 by any appropriate means such as rotary screen, rotogravure or flexographic printing or by encapsulating the thermocromatic compositions in a clear polymer such as, but not limited to, polyvinyl chloride, polyvinylodine chloride, cellulose acetate, polyethylene, cellophane and the like which can then be laminated to the substrate. The adhesive layer 16 may then be subsequently applied via, for example, kiss coating, spraying, foaming or any other means of application which is capable of applying the adhesive on one surface without affecting the other surface. Alternatively, the adhesive layer 16 can be provided on the substrate 12 prior to treating with the thermocromatic composition.

Obviously, the substrate 12 may also be imprinted with any desired aesthetic design or other indicia. The device may be dye cut or laser cut into any desired shape. Further, it should be appreciated that the device may be provided as a continuous roll, on a card in a clear polyethylene bag for display or in any other appropriate desired manner.

As noted above, the device 10 allows for the monitoring of body temperature of an animal such as, for example, a human, an equine athlete or other animal where the monitoring of body temperature is desired for any reason. Thus, the method of monitoring of the present invention comprises positioning a thermocromatic device 10 into intimate contact with the skin of the animal wherein the thermocromatic device changes color at a predetermined temperature indicative of a temperature related physical condition to be detected. The method includes adhering the thermocromatic device 10 to the skin or elastically biasing the thermocromatic device into close engagement with the skin. Further, the method includes using a flexible substrate in the thermocromatic device that is capable of following the surface of the skin during bodily movements.

The device 10 and associated method have a number of applications and uses including, but not limited to, monitoring body temperature as an indication of potential for hyperthermia or hypothermia. Thus, the device may be used by coaching staffs, trainers and athletes and military personel as a tool to indicate a raised potential for hyperthermia. For this application, the thermocromatic composition incorporates a thermocromatic agent that undergoes a color change between about 99°-101° F. or between about 100°-101° F. or at about 100° F.

Similarly, where the device is used to detect a potential for hypothermia, the device incorporates a thermocromatic composition 14 having a thermocromatic agent that changes color between about 95°-97° F. or at about 96° F. Thus, for these human applications it should be appreciated that the thermocromatic composition changes color at a predetermined temperature between about 95° F. and about 101° F. However, for non-human applications relating to animals with a higher normal temperature (i.e. dogs and horses), the predetermined temperature range may run as high as 105° F. or even higher.

Other potential applications for the device 10 and related method include monitoring body temperature as an indication of potential ovulation in a woman, monitoring body temperature as an indication of potential ovulation in a horse, monitoring body temperature of a horse to determine potential overheating, heat exhaustion/heat stress as well as in various thermography applications.

Thermography has been used to aid in diagnosing long term pain. Local skin temperature generally increases due to dilation of the blood vessels: however over a long period of time the temperature can drop. The difference can range from 2° to 7° F.

Thermal abnormalities are generally manifested as pain and the present invention can be used to estimate or pinpoint the affected area. Deep vein thrombosis is linked with pulmonary embolism and because a deep vein thrombosis will show a higher temperature and a slower cooling rate in the affected limb, this affect can be measured utilizing the present invention. Further, conditions that affect peripheral circulation generally show a lowering of temperature. Insufficient blood flow to the brain can be measured by thermography. Damaged main arteries cause redirection of blood flow through vessels very close to the skin. Thermography can be used to detect the growth of tumors in breast tissue. Due to the increase in metabolic rate in an active tumor and the change of blood supply, the result is an increase in temperature which can be measured and compared to other unaffected areas of the breasts. Thus, the device of the present invention also has potential application in these medical applications.

The following examples are presented to further illustrate the invention, but it is not to be considered as limited thereto.

EXAMPLE 1

One composition useful in the present invention involved screen printing a 95% cotton and 5% spandex circular knit fabric with a combination of cholesteric and chiral nematic inks. These inks were set by specific combination to transition from a clear color to a high visibility yellow color. This combination of cholesteric and chiral nematic inks can also be printed via rotogravure, flexographic and rotary and flat bed screen upon other substrates such as nylon, nylon/spandex, polyester, polyester/spandex, wool, silk, rayon or combinations of these fibers. Other substrates can be, but are not limited to, polyvinyl chloride, polyvinylydene chloride, cellophane, ethyl vinyl acetate. Other high visibility colors can be achieved by combining these liquid crystal thermochromic inks to achieve bright reds, oranges and limes. The carrier, in this case, was water. The thermochromic ink composition included a combination of cholesteric and chiral nematic inks in amounts ranging from about 0.1% to about 5.0% of each. In this specific example the 3.3% cholesteric ink and 2.4% chiral nematic ink was used. The negatively charged ionizing agent is incorporated in an amount ranging from about 0.5% to about 1.0% and the remainder is the carrier. In this specific example 0.5% food grade diatomite (86% silica/5% sodium/3% magnesium/2% iron) was used. The thermochromic ink was rotary screen printed, using a sufficient number of passes (between 1 and 5) to deliver a wet thickness of 150-300 microns (6-12 mils) which will dry to approximately 50-100 microns (2-4 mils).

EXAMPLE NO. 2

Another useful composition involved screen printing, although rotogravure and flexographic printing can be used, leuco dyes comprised of crystal violet lactones, spirolactones, fluorans and spiropyrans and combinations of these. The 95% cotton and 5% spandex base fabric was a circular knit fabric and it was dyed into a shade of high visibility yellow using fiber reactive dyestuffs. The dyed fabric was over-printed with a Black liquid crystal thermochromic ink which clears or disappears at 100° F. to 101° F., showing the high visibility color underneath. The carrier, in this case, was water.

This composition included a combination leuco dyestuffs in the amount of 2.0% spirolactone and 1.0% spiropyran. The negatively charged ionizer, food grade diatomite, was incorporated at about 0.5% to about 1.0% and the remainder was carrier. This composition was rotary screen printed, using a sufficient number of passes to achieve good coverage and to deliver a wet thickness of about 150-300 microns (6-12 mils) which will dry to approximately 50-100 microns (2-4 mils).

EXAMPLE NO. 3

Another useful composition involved dispersing a combination of leuco dyes in a thermoplastic film such as polyvinyl chloride. The film thickness was 15 mils but the film thickness can be adjusted through extrusion to a range of 1 mil up to 20 mils or more. The leuco dyes employed here were mixtures of spirolactones and spiropyrans. These dyes were combined so that the color would clear or disappear at 100° to 101° F. The carrier, in this case, was a polyol.

This composition was achieved by dispersing 2.5% spirolactone leuco dyes and 2.5% spiropyran leuco dyes into the following formulation:

52% polyvinyl chloride powder;
44% plasticizer (the plasticizer was diisononyl phthalate but it can also be dioctyl phthalate);
3.0% TIXB (2,2,4-Trimethyl-1,3-pentanediol diisobutyrate); and
About 0.5% negatively charged ion donor (food grade diatomite).

The film was extruded to a 15 mil thick sheet.

EXAMPLE NO. 4

Another useful composition involves dispersing a combination of liquid crystal thermochromic inks, made from cholesteric inks and chiral nematic inks in such a way that the color changed at 100° F. to 101° F., into a thermoplastic film such as polyvinyl chloride, using a polyol as the carrier.

The combination of inks can run between about 0.1% to about 5.0%. The inks would then be dispersed into the liquid polyvinyl chloride batch using the following formulation:

52% polyvinyl powder;
44% plasticizer (the plasticizer can be diisononyl phthalate or dioctyl phthalate);
3.0% TIXB (2,2,4-Trimethyl-1,3-pentanediol diisobutyrate);
About 0.5% to about 1.0% negatively charged ion donor.

EXAMPLE NO. 5

Examples 3 and 4 can use a variety of thermoplastic polymers such as polyvinylydene chloride, ethyl vinyl acetate, cellophane, polystyrenes and polycarbonates and neoprenes and urethanes as substrates into which liquid crystal thermochromic inks or leuco dyes can be dispersed using either water or a polyol as the carrier.

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A thermocromatic device for detecting body temperature, consisting of:
   a substrate; and
   a thermocromatic composition on said substrate, said thermocromatic composition consisting of (a) between 0.1 and 5.0 weight percent of a thermocromatic agent that changes color at a predetermined temperature indicative of a temperature related condition to be detected, (b) between 0.5 and 1.0 weight percent negatively charged ionizing agent and (c) a remainder carrier selected from a group consisting of water, alcohols, polyols, phthalates and mixtures thereof wherein said negatively charged ionized agent is selected from a group consisting of diatomaceous earth, choline chloride, modified polyolefins and mixtures thereof.

2. The device of claim 1, further including an adhesive for positively securing said substrate to skin on a body to be monitored.

3. The device of claim 1, wherein said thermocromatic agent is selected from a group consisting of a thermocromatic ink, a thermocromatic liquid crystal ink, a chiro nematic liquid crystal ink, cholesteryl nonanoate, a cyanobisphenyl, a combination of sholesteryl and nematic inks, a mixture of leuco dyes with a weak acid, a mixture of crystal violet lactone, a spirolactone, a fluoran, a spiropyran, a fulgide or a fulgide with bisphenol A, a paraben, octadecylphosphoric acid, a 1,2,3-triazole derivative or 4-hydroxycoumarin, a mineral oxide, zinc oxide, lead oxide, cuprous mercury iodide, mercury iodide, nickel sulfate, a chromium rich pyrope, a chrystalline bismuth oxychloride, an organosiloxane containing methacryloyl or actyloyl functional groups, an organosiloxane containing nuclei that are divalent radicals consisting of 1,4 phenylene, 1,4 cyclohexylene, 2,2 pyridinylene, 2,5 pyranylene, 5,2 pyrimidinylene, 2,5-(1,3-dioxanylene), 2,6-naphthylidene and 1,4-naphylidene and combinations thereof.

4. The device of claim 1, wherein said substrate is woven, knit or non-woven.

5. The device of claim 1, wherein said substrate is selected from a group of materials consisting of a natural fiber, a synthetic fiber, cotton, polyester, nylon, rayon, silk, wool, cotton blends, polyester blends and mixtures thereof.

6. The device of claim 2, wherein said adhesive is selected from a group consisting of flexible silicones, epoxies, acrylics and mixtures thereof.

7. The device of claim 1, wherein said substrate takes a form selected from a group consisting of a patch, a scarf, a shirt, a headband, a wrist band, a sweat band, a tee shirt, a compression jersey, a necklace and a pair of compression shorts.

8. The device of claim 1, wherein said predetermined temperature is between 95°-101° F.

9. The device of claim 1, wherein said predetermined temperature is between 99°-110° F.

10. The device of claim 1, wherein said predetermined temperature is between 100°-101° F.

11. The device of claim 1, wherein said predetermined temperature is 100° F.

12. The device of claim 1, wherein said predetermined temperature is between 95°-97° F.

13. The device of claim 1, wherein said predetermined temperature is 96° F.

* * * * *